United States Patent [19]

Jorgenson et al.

[11] Patent Number: 5,115,131
[45] Date of Patent: May 19, 1992

[54] MICROELECTROSPRAY METHOD AND APPARATUS

[75] Inventors: James W. Jorgenson; Daniel M. Dohmeier, both of Chapel Hill, N.C.

[73] Assignee: The University of North Carolina at Chapel Hill, Chapel Hill, N.C.

[21] Appl. No.: 700,572

[22] Filed: May 15, 1991

[51] Int. Cl.⁵ .................... B01D 59/44; A01J 49/00
[52] U.S. Cl. ................................. 250/288; 250/282
[58] Field of Search ................ 250/288, 281, 282

[56] References Cited

U.S. PATENT DOCUMENTS

| | | | |
|---|---|---|---|
| 4,531,056 | 7/1985 | Labowsky et al. | 250/288 |
| 4,542,293 | 9/1985 | Fenn et al. | 250/288 |
| 4,842,701 | 6/1989 | Smith et al. | 250/288 |
| 4,861,988 | 8/1989 | Henion et al. | 250/282 |
| 4,885,076 | 12/1989 | Smith et al. | 250/288 |
| 4,935,624 | 6/1990 | Henion et al. | 250/288 |
| 4,977,320 | 12/1990 | Chowdhury et al. | 250/288 |
| 4,994,165 | 2/1991 | Lee et al. | 204/180.1 |
| 5,015,845 | 5/1991 | Allen et al. | 250/288 |

OTHER PUBLICATIONS

M. Ikonomou et al., *Anal. Chem.* 62, 957 (1990).
M. Mann, *Organ. Mass Spec.* 25, 575 (1990).
R. Smith, *Anal. Chem.* 60, 1948 (1988).
R. Smith et al., *Anal. Chem.* 62, 885 (1990).

*Primary Examiner*—Bruce C. Anderson
*Attorney, Agent, or Firm*—Bell, Seltzer, Park & Gibson

[57] ABSTRACT

A method of generating an electrospray from a solution is disclosed which is useful for electrospraying at low flow rates, for electrospraying directly into a vacuum, or both. The method comprises the steps of causing the solution to flow through a capillary tube to an outlet opening formed in the terminal portion thereof. The capillary tube terminal portion has an inner diameter of not more than 50 micrometers and an outer diameter of not more than 150 micrometers. An electrical potential difference is provided between the capillary tube terminal portion and a conductor spaced from said terminal portion, with the potential sufficient to cause the solution to electrospray from the capillary outlet.

The method is particularly useful for detecting analytes in the solution being electrosprayed by mass spectral analysis.

25 Claims, 2 Drawing Sheets

MICROELECTROSPRAY METHOD AND APPARATUS

This invention was made with Government support under grant number RO1 GM39515 from the National Institutes of Health. The Government may have certain rights to this invention.

FIELD OF THE INVENTION

The invention relates to electrospray in general, and particularly relates to methods and apparatus for carrying out electrospray at low flow rates directly into a vacuum.

BACKGROUND OF THE INVENTION

The electrical spraying of liquids to produce ions, termed electrospray, was first used as a tool in analytical chemistry in the late 1960's. This initial work was not expanded upon until 1984, when John Fenn and co-workers reported combining electrospray ionization and mass spectrometry (ESI/MS) to analyze high molecular weight species. See, e.g., U.S. Pat. No. 4,542,293 to J. Fenn et al.; U.S. Pat. No. 4,531,056 to M. Labowsky et al.

A major limitation of current electrospray technology is that the electrospray is performed at atmospheric pressure. See, e.g., U.S. Pat. No. 4,977,320 to Chowdhury et al.; U.S. Pat. No. 4,935,624 to Henion et al.; U.S. Pat. No. 4,885,076 to Smith et al.; U.S. Pat. No. 4,842,701 to Smith et al. This creates a need for differential pumping and reduces sampling efficiency. See M. Ikonomou et al., *Anal. Chem.* 62, 957 (1990); M. Mann, *Organ. Mass Spec.* 25, 575 (1990). A further problem is that high flow rates (e.g., above 0.5 μl/minute) have been required. R. Smith et al., *Anal. Chem.* 60, 1948 (1988).

In view of the foregoing, objects of the present invention are to provide a way to electrospray directly into a vacuum, and a way to electrospray at low flow rates.

SUMMARY OF THE INVENTION

The foregoing and other objects and advantages are provided by a method of generating an electrospray from a solution. The method comprises the steps of causing the solution to flow through a capillary tube to an outlet opening formed in the terminal portion thereof. The capillary tube terminal portion has an inner diameter of not more than 50 micrometers and an outer diameter of not more than 150 micrometers. An electrical potential difference is provided between the capillary tube terminal portion and a conductor spaced from said terminal portion, with the potential sufficient to cause the solution to electrospray from the capillary outlet.

A particular embodiment of the present invention comprises a method of detecting an analyte by mass spectral analysis in a solution containing the analyte. The method comprises causing the solution to flow through a capillary tube to an outlet opening formed in the terminal portion thereof, the capillary tube terminal portion having an inner diameter of not more than 50 micrometers and an outer diameter of not more than 150 micrometers. The ambient pressure at said capillary outlet is maintained at less than 10 millitorr. An electrical potential difference is provided between the capillary tube terminal portion and a conductor spaced from the terminal portion, with the potential sufficient to cause the solution to electrospray from the capillary outlet and ionize the analyte in the solution. The ionized analyte is then detected by mass spectral analysis.

An apparatus of the present invention for generating an electrospray from a solution comprises a capillary tube having a terminal portion and an outlet opening formed in the terminal portion, with the capillary tube terminal portion having an inner diameter of not more than 50 micrometers and an outer diameter of not more than 150 micrometers. A chamber (e.g., a vacuum chamber) is included which contains the capillary tube terminal portion, the vacuum chamber further containing a conductor spaced from the capillary tube terminal portion. A Power supply is provided for maintaining an electrical potential difference between the capillary tube terminal portion and the conductor spaced from the terminal portion, with the potential sufficient to cause the solution to electrospray from the capillary outlet. Preferably, the apparatus also includes a pump for maintaining the ambient pressure in the chamber at less than 10 millitorr. The chamber also preferably contains a mass spectrometer. The aforesaid conductor may comprise a mass spectrometer entrance lens.

DETAILED DESCRIPTION OF THE PREFERRED EMBODIMENTS

The present invention may be used to detect a variety of different analytes, including (but not limited to) proteins, peptides, polynucleic acids, fats, lipids, sugars, carbohydrates, synthetic polymers, metal ions, and small ions. In general, any analyte which is soluble in a polar or moderately polar solvent solution can be employed.

Suitable solvent solutions include, but are not limited to, water, methanol, acetonitrile, and mixtures thereof. The solvent solution may be caused to flow in the capillary at a rate of from 0.1 to 100 nanoliters per second. Preferred are flow rates of from 0.1 to 10 nanoliters per second, with flow rates of 1 nanoliter per second being typical.

Figure 1:
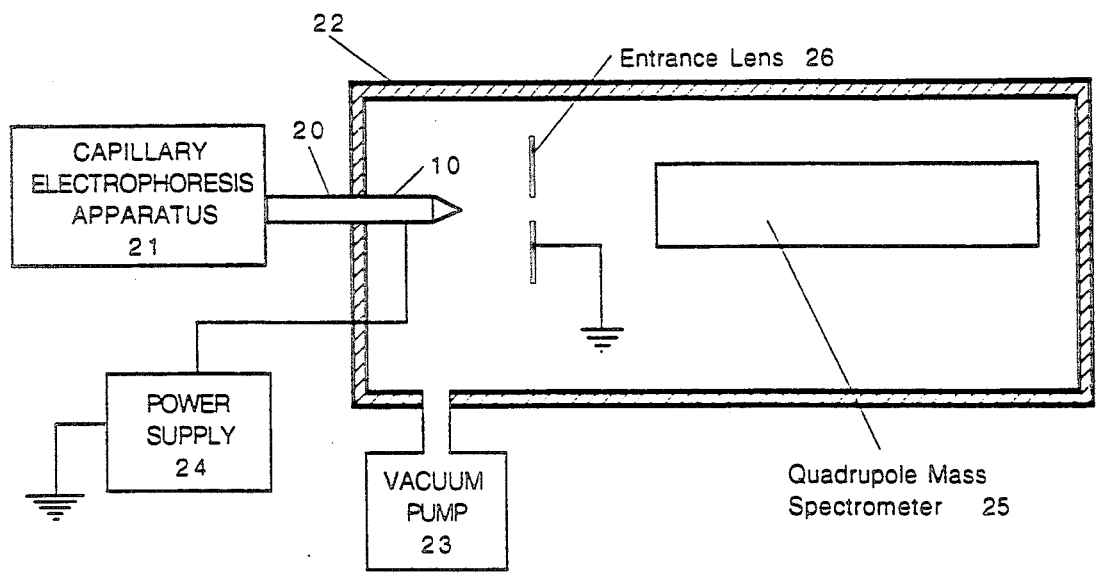
FIG. 1 is a schematic diagram of an apparatus of the present invention.

An apparatus of the present invention is shown schematically in FIG. 1 The electrospray capillary 10 is comprised of the downstream end of the capillary electrophoresis capillary 20 of a capillary electrophoresis apparatus 21. The electrospray capillary terminates in a vacuum chamber 22, to which is connected a vacuum pump 23 for evacuating the chamber. A power supply 24 is electrically connected to the electrospray capillary and ground. A commercial tandem triple quadrupole mass spectrometer 25 is provided in the vacuum chamber, and the entrance lens 26 of the mass spectrometer is electrically connected to ground. The entrance lens is spaced from the electrospray capillary 10 so that the electrospray emanating from the electrospray capillary is directed towards the mass spectrometer 25.

The establishment of a potential which will produce an electrospray can be carried out in accordance with known procedures. The electrospray capillary can be held at +1,200 volts with respect to ground. Higher voltages may be employed, and spray may also be seen at lower voltages (e.g., +800 volts). The capillary may be held at a negative potential, but this is less preferred.

The pressure in the vacuum chamber should be held at a pressure suitable for mass spectrometry, such as 2 microtorr. The present invention, however, has utility for applications other than mass spectrometry, and thus may in general be carried out at pressures less than 10 millitorr (e.g., less than 1 millitorr; less than 0.1 millitorr). If electrospray into a vacuum is not required for a particular application, then the tip of the present invention may also be employed to electrospray into higher ambient pressures, such as 10 torr and above, including atmospheric pressure (760 torr). Ambient pressures of from 10 millitorr to 10 torr tend to be less preferred because of the glow discharges which occur on electrospraying solutions at these pressures, though this may not necessarily be deleterious for all applications.

Figure 2:
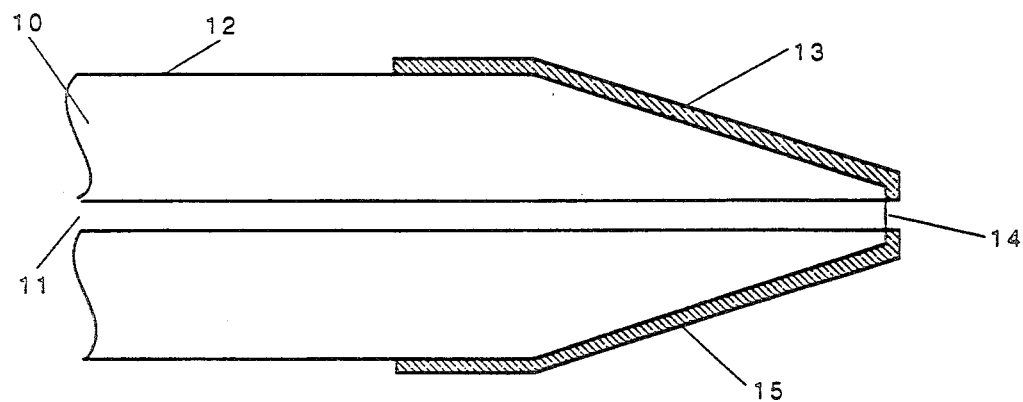
FIG. 2 is a schematic diagram of an electrospray capillary of the present invention.

An electrospray capillary of the present invention is schematically illustrated in FIG. 2. The electrospray capillary 10 has a capillary bore 11 formed therein through which the solution to be electrosprayed flows. The capillary tapers from an intermediate region 12 of large diameter to a terminal portion 13 of relatively smaller diameter. The terminal portion has an outlet opening 14 for the capillary bore 11 formed in the tip 15 thereof from which the electrospray emanates.

The terminal portion 13 inner diameter, which defines the outlet opening 14, is generally not greater than 50 micrometers, and is preferably not greater than 20 micrometers. The inner diameter of the terminal portion need only be sufficiently large to enable an electrospray to emanate therefrom and can be as small as 1 or 2 microns in diameter. Currently preferred are tips having an inner diameter at the terminal portion of between 5 and 20 micrometers. The inner diameter of the capillary intermediate portion may optionally be greater than the inner diameter of the capillary terminal portion, with the inner diameter tapering and decreasing from the intermediate portion to the terminal portion, if desired for particular applications (e.g., with capillary electrophoresis capillaries, which have bores of 50 to 70 micrometers).

The capillary tube terminal portion 13 preferably has an outer diameter of not more than 150 micrometers, and more preferably has an outer diameter of not more than 100 micrometers. The lower limit to the outer diameter will depend upon the particular material from which the tip is fabricated, but may be as low as 5, 10, or 20 micrometers. Currently preferred are capillary tubes having a terminal portion with an outer diameter of from about 50 to about 70 micrometers. The outer diameter of the capillary tube illustrated decreases from the intermediate portion to the terminal portion, forming an elongate tapered region having a cone half angle of about 10 to 20 degrees.

An electrospray capillary used to carry out the present invention can be made of any suitable conductive material, such as steel, conducting polymers, fused silica, and glass (e.g., soda lime glass, borosilicate glass). Tips constructed of fused silica or glass are metallized with a material such as gold, silver, or platinum by processes such as sputtering or vapor deposition. A metal layer 15 is illustrated in FIG. 2.

Figure 3:
FIG. 3 is an electron micrograph showing the side view of an electrospray capillary of the present invention, particularly illustrating the taper of the capillary to a small diameter terminal portion.
Figure 4:
FIG. 4 is an electron micrograph showing the terminal portion of an electrospray capillary of the present invention, particularly showing the outlet opening from which the solution is electrosprayed.

A metallized borosilicate glass capillary tube for use in carrying out the present invention can be fabricated in a routine manner. In a preferred embodiment of the invention, PYREX 7740 TM tubing having an internal diameter (i.d.) of 0.2032 millimeters and an outer diameter (o.d.) of 5 to 6 millimeters is purchased from Wilmad Glass, Buena, N.J., USA, and drawn on a Shimadzu GDM 1B drawing machine at a draw ratio of 160. One end of a one meter section of drawn capillary tubing is immersed to a depth of 2 millimeters in 10 to 20 milliliters of 48% aqueous hydrogen fluoride solution and etched, with stirring, for about twenty minutes. During etching, water is pumped through the tubing into the etch bath at a velocity of about 1 centimeter per second to prevent etching of the interior of the capillary tube. The etched capillary tip is then coated with gold by ohmically heating a gold wire in a bell jar with the tip under a vacuum, in accordance with known procedures. An electron micrograph of a tip produced in essentially this manner is shown in FIG. 3 and FIG. 4.

The electrospray apparatus of the present invention can be directly operatively associated with a mass analyzer such as a commercial quadrupole mass spectrometer for mass spectrometric analysis of analytes by modification of known procedures, such as described in U.S. Pat. Nos. 4,977,320; 4,935,624; 4,885,076; 4,842,701; 4,542,293; and 4,531,056, in light of the instant disclosure. Applicants specifically intend that the disclosures of these and all other patent references cited herein be incorporated herein by reference. As noted above, the present invention eliminates the need for skimmers and differential pumping when electrospraying into the mass analyzer, as the electrospray may be carried out directly into a vacuum. As an alternative to mass spectroscopy, ions formed by electrospray into a vacuum in accordance with the present invention may be analyzed by other vacuum spectroscopy means, including but not limited to laser spectroscopy, flame spectroscopy, atomic spectroscopy, and ion traps.

In the present invention, the electrospray capillary can comprise any sample delivery capillary, including the downstream end of a capillary liquid chromatography capillary or a capillary electrophoresis capillary. Capillary electrophoresis includes variations such as capillary zone electrophoresis, electrokinetic chromatography and isotachophoresis. An electrospray apparatus of the present invention can be operatively associated with a capillary electrophoresis apparatus in accordance with known procedures, such as shown in U.S. Pat. Nos. 4,885,076 and 4,842,701 to R. Smith et al.; and can be operatively associated with a liquid chromatography apparatus in accordance with known procedures, such as shown in U.S. Pat. No. 4,935,624 to Henion et al. The present invention, however, eliminates the need for a sheath electrode liquid or a make-up flow, hence the solution which is electrosprayed consists essentially of the solution subjected to capillary liquid chromatography or capillary electrophoresis The foregoing is illustrative of the present invention, and not to be construed as limiting thereof. The invention is defined by the following claims, with equivalents of the claims to be included therein.

That which is claimed is:

1. A method of generating an electrospray from a solution, comprising:

causing said solution to flow through a capillary tube to an outlet opening formed in the terminal portion thereof, said capillary tube terminal portion having an inner diameter of not more than 50 micrometers and an outer diameter of not more than 150 micrometers;

providing an electrical potential difference between said capillary tube terminal portion and a conductor spaced from said terminal portion, with said potential sufficient to cause said solution to electrospray from said capillary outlet.

2. A method according to claim 1, wherein said capillary tube terminal portion has an inner diameter of not more than 20 micrometers.

3. A method according to claim 1, wherein said capillary tube terminal portion has an outer diameter of not more than 100 micrometers.

4. A method according to claim 1, further comprising the step of maintaining the ambient pressure at said capillary outlet at less than 10 millitorr.

5. A method according to claim 4, wherein the ambient pressure at said capillary outlet is maintained at less than 1 millitorr.

6. A method according to claim 4, wherein the ambient pressure at said capillary outlet is maintained at less than 0.1 millitorr.

7. A method according to claim 1, wherein said capillary tube comprises a capillary electrophoresis capillary.

8. A method according to claim 1, wherein said capillary tube comprises a capillary liquid chromatography capillary.

9. A method according to claim 1, wherein said solution is caused to flow in said capillary tube at a rate of 0.1 to 100 nanoliters per second.

10. A method according to claim 1, wherein said solution is caused to flow in said capillary tube at a rate of 1 to 10 nanoliters per second.

11. A method of detecting an analyte by mass spectral analysis in a solution containing said analyte, comprising:

causing said solution to flow through a capillary tube to an outlet opening formed in the terminal portion thereof, said capillary tube terminal portion having an inner diameter of not more than 50 micrometers and an outer diameter of not more than 150 micrometers;

maintaining the ambient pressure at said capillary outlet at less than 10 millitorr;

providing an electrical potential difference between said capillary tube terminal portion and a conductor spaced from said terminal portion, with said potential sufficient to cause said solution to electrospray from said capillary outlet and ionize said analyte in said solution; and detecting said ionized analyte by mass spectral analysis.

12. A method according to claim 11, wherein said capillary tube comprises a capillary electrophoresis capillary.

13. A method according to claim 12, wherein said solution is subjected to capillary electrophoresis prior to said electrospray step, and wherein said solution which is electrosprayed consists essentially of said solution subjected to capillary electrophoresis.

14. A method according to claim 11, wherein said capillary tube comprises a capillary liquid chromatography capillary.

15. A method according to claim 14, wherein said solution is subjected to capillary liquid chromatography prior to said electrospray step, and wherein said solution which is electrosprayed consists essentially of said solution subjected to capillary liquid chromatography.

16. A method according to claim 11, wherein said capillary tube terminal portion has an inner diameter of not more than 20 micrometers.

17. A method according to claim 11, wherein said capillary tube terminal portion has an outer diameter of not more than 100 micrometers.

18. A method according to claim 11, wherein the ambient pressure at said capillary outlet is maintained at less than 1 millitorr.

19. A method according to claim 11, wherein the ambient pressure at said capillary outlet is maintained at less than 0.1 millitorr.

20. A method according to claim 11, wherein said solution is caused to flow in said capillary tube at a rate of 0.1 to 100 nanoliters per second.

21. An apparatus for generating an electrospray from a solution, comprising:

a capillary tube having a terminal portion and an outlet opening formed in said terminal portion, said capillary tube terminal portion having an inner diameter of not more than 50 micrometers and an outer diameter of not more than 150 micrometers;

a vacuum chamber containing said capillary tube terminal portion, said vacuum chamber further containing a conductor spaced from said capillary tube terminal portion; and power supply means for providing an electrical potential difference between said capillary tube terminal portion and said conductor spaced from said terminal portion, with said potential sufficient to cause said solution to electrospray from said capillary outlet.

22. An apparatus according to claim 21, further comprising pump means for maintaining the ambient pressure in said vacuum chamber at less than 10 millitorr.

23. An apparatus according to claim 21, said vacuum chamber further containing a mass spectrometer, and wherein said conductor comprises a mass spectrometer entrance lens.

24. An apparatus according to claim 21, wherein said capillary tube terminal portion has an inner diameter of not more than 20 micrometers.

25. An apparatus according to claim 21, wherein said capillary tube terminal portion has an outer diameter of not more than 100 micrometers.

* * * * *

UNITED STATES PATENT AND TRADEMARK OFFICE
CERTIFICATE OF CORRECTION

PATENT NO. : 5,115,131

DATED : May 19, 1992

INVENTOR(S) : James W. Jorgenson; Daniel M. Dohmeier

It is certified that error appears in the above-identified patent and that said Letters Patent is hereby corrected as shown below:

Column 5, line 41, please change "1" to --0.1--.

Signed and Sealed this

Thirteenth Day of July, 1993

Attest:

MICHAEL K. KIRK

Attesting Officer — Acting Commissioner of Patents and Trademarks